United States Patent
Waizenegger

(10) Patent No.: US 9,220,551 B2
(45) Date of Patent: Dec. 29, 2015

(54) CLAMPING ELEMENT FOR SETTING A BONE FRACTURE AND FIXATION DEVICE COMPRISING SAME

(75) Inventor: Markus Waizenegger, Mühlheim a.d. Donau (DE)

(73) Assignee: HIPP MEDICAL AG, Kolbingen (DE)

( * ) Notice: Subject to any disclaimer, the term of this patent is extended or adjusted under 35 U.S.C. 154(b) by 169 days.

(21) Appl. No.: 14/002,245

(22) PCT Filed: Jan. 25, 2012

(86) PCT No.: PCT/EP2012/000330
§ 371 (c)(1),
(2), (4) Date: Oct. 25, 2013

(87) PCT Pub. No.: WO2012/116773
PCT Pub. Date: Sep. 7, 2012

(65) Prior Publication Data
US 2014/0046387 A1 Feb. 13, 2014

(30) Foreign Application Priority Data
Mar. 2, 2011 (DE) .......................... 10 2011 001 018

(51) Int. Cl.
| A61B 17/04 | (2006.01) |
| A61B 17/84 | (2006.01) |
| A61F 2/08 | (2006.01) |
| A61B 17/68 | (2006.01) |
| A61B 17/86 | (2006.01) |

(52) U.S. Cl.
CPC ............... *A61B 17/84* (2013.01); *A61B 17/685* (2013.01); *A61B 17/842* (2013.01); *A61B 17/86* (2013.01); *A61B 17/8695* (2013.01); *A61B 2017/681* (2013.01)

(58) Field of Classification Search
CPC ...... A61B 17/84; A61B 17/842; A61B 17/86; A61B 17/685; A61B 17/8004; A61B 17/82; A61B 2017/681; A61B 17/8071; A61B 17/8057; A61B 17/8023; A61B 17/7047; A61B 17/7004
USPC .......................................... 606/902–906, 324
See application file for complete search history.

(56) References Cited

U.S. PATENT DOCUMENTS

| 5,387,213 A | 2/1995 | Breard et al. |
| 6,506,191 B1 * | 1/2003 | Joos ............................ 606/86 B |

(Continued)

FOREIGN PATENT DOCUMENTS

| DE | 1600676 U | 2/1950 |
| EP | 0498709 A1 | 8/1992 |

(Continued)

*Primary Examiner* — Kevin T Truong
*Assistant Examiner* — Si Ming Ku
(74) *Attorney, Agent, or Firm* — Abel Law Group, LLP

(57) ABSTRACT

Disclosed is a clamping element for setting a bone fracture. The element features a flexible and substantially non-plastically deformable continuous loop inside which at least two fixing elements can be pushed through, and an extension element of alterable length that can be inserted into and is expandable inside the continuous loop in such a manner that in order to enable the extension element to apply forces directed towards each other to the fixing elements, a predetermined tensile stress can be generated over the circumference of the continuous loop. Also disclosed is a setting device having the clamping element.

20 Claims, 3 Drawing Sheets

(56) References Cited

U.S. PATENT DOCUMENTS

| | | |
|---|---|---|
| 7,927,356 B2 | 4/2011 | Lim |
| 8,029,541 B2 | 10/2011 | Alamin et al. |
| 8,226,693 B2 | 7/2012 | Reimels et al. |
| 8,454,660 B2 | 6/2013 | Alamin et al. |
| 2006/0106381 A1* | 5/2006 | Ferree et al. ............ 606/61 |
| 2007/0233074 A1* | 10/2007 | Anderson et al. ............ 606/61 |
| 2007/0293863 A1 | 12/2007 | Reimels et al. |
| 2008/0021459 A1* | 1/2008 | Lim ............ 606/61 |
| 2008/0154312 A1* | 6/2008 | Colleran et al. ............ 606/283 |
| 2008/0177264 A1 | 7/2008 | Alamin et al. |
| 2009/0036930 A1 | 2/2009 | Allison |
| 2011/0060372 A1 | 3/2011 | Allison |
| 2011/0184467 A1 | 7/2011 | Lim |
| 2011/0295318 A1 | 12/2011 | Alamin et al. |

FOREIGN PATENT DOCUMENTS

| | | |
|---|---|---|
| WO | 2005065557 A1 | 7/2005 |
| WO | 2008006098 A2 | 1/2008 |
| WO | 2008051806 A2 | 5/2008 |

* cited by examiner

CLAMPING ELEMENT FOR SETTING A BONE FRACTURE AND FIXATION DEVICE COMPRISING SAME

BACKGROUND OF THE INVENTION

1. Field of the Invention

The invention relates to a clamping element for setting or fixation of a bone fracture as well as to a setting or fixation device comprising such a clamping element.

2. Discussion of Background Information

When a bone fracture is immobilized insufficiently, a callus formation, i.e. a tyloma-like thickening of the ends of the fracture from overgrowing bone tissue, can occur. In order to avoid such an indirect fracture healing via a callus, bone plates are used which are applied and attached to the outer surface of a broken bone so that the fracture site is set, i.e. fixed, during the healing process.

For such applications for the treatment of bone fractures, from prior art there are mainly known rigid, metallic bone plates formed in a planar manner and having bores which are screwed at the opposite sides of a fracture. For the fastening of such settings or fixations, usually so-called cortical screws are used which are screwed into the outer bone tissue, the so-called cortical layer, which has the highest strength of the bone. The setting or fixation ensures that the ends of the fracture cannot move with respect to each other and that newly formed bone tissue can accumulate such that it will not be subjected to any loads.

Furthermore, it is assumed that the healing process of a fracture can be influenced beneficially when a compression is applied onto the joined fracture site. Thereby, a particularly close adaption, i.e. a very small clearance over which the ends of the fracture grow towards each other again, is effected.

In order to obtain said desired function, the published patent application US 2008/0154312 A1 discloses a two-part bone plate, the two halves of which can move towards each other by means of an axial guide. For the creation or production of a compression, in various embodiments a band-shaped elastomeric member is provided which is stretched around the halves.

The published patent application US 2007/0293863 A1 describes a bone bridge having two plate-shaped elements for receiving bone screws through which an elastic cable extends.

Such simple constructions of elastic bone plates or bridges have the disadvantage that the pretension cannot be readjusted. If necessary, a stepwise adaptation can be provided by a staggered selection of elastic elements of different lengths or different stress-strain curves. An exact adaptation of the pretension with respect to dimensional tolerances of fastening points, however, is impossible.

A defined pretension is of importance with regard to the coordination of several settings, in particular of mutually opposing settings, as well as with regard to indifferent fracture margins, in order to ensure an exact alignment of the fracture ends with respect to each other during the entire healing process.

Accordingly, when the above-mentioned devices are used, the fixing means have to be placed into the bone in a surgical operation very accurately as regards position. Furthermore, due to the course of the fracture lines and due to the anatomic conditions, in practice the distance of the fixing means is not always freely selectable.

Furthermore, a system with an elastic principle of action, i.e. with a distinctive stress-strain curve, will always exhibit the following disadvantages:

The relationship between that pretension which is required for an effective fixing of the position against external forces acting thereupon and that force which acts upon the fracture ends for the adaption due to the same pretension is directly dependent on the stress-strain curve of the used elastic element. In other words, for an effective setting or fixation of fracture sites onto which, due to anatomic conditions, a large leverage acts during body movements, as is for instance the case for tubular bones at the arms or the legs, a correspondingly high pretension is required in order to reliably prevent a deflection of the fracture site by potential forces acting thereupon.

Said pretension of an elastic element, which is determined by its function, will, however, permanently apply a possibly unfavourably high pressure onto the bone tissue of the fracture site.

In this connection, elastic elements with a correspondingly short and steep stress-strain curve have more favourable properties with respect to the pretension for a compression and their suitability for the fixing in a stable position. On the other hand, they are more sensitive to dimensional tolerances of the fastening points. Rigid bone plates uncouple said two properties so that a desired compression of the ends of the fracture fails to appear.

Therefore, the invention is based on the object to provide a clamping element for a setting or fixation device, which clamping element provides a very good and stable fixing of the position against outer forces as well as an adjustable compression of the fracture which can be adapted individually to fastening points which are conditioned by the fracture or by the anatomy, and which can nevertheless be produced at particularly low costs, in order to expand the field of application of compression-producing settings. Moreover, the invention is also based on the object to provide a setting or fixation device in which the clamping element is used.

SUMMARY OF THE INVENTION

The object is solved by the clamping element as well as by the setting or fixation device set forth in the appended claims.

The clamping element according to the invention comprises a flexible and substantially non-plastically deformable continuous loop, inside which at least two fixing means, preferably cortical screws, can be pushed through, and an extension element of alterable length that can be inserted into and is expandable inside the continuous loop in such a manner that in order to enable the extension element to apply forces to the fixing means, said forces being directed towards each other, a predetermined tensile stress can be generated over the circumference of the continuous loop.

By a lengthening of the extension element, the continuous loop experiences a transverse contraction, while the circumference remains constant, and, consequently, effects a pretension between the surrounded fixing means, said pretension being directed towards each other. As the continuous loop is relatively inelastic, i.e. has a short and steep stress-strain curve, a secure and stable fixing of the position with respect to forces acting thereupon from the outside is guaranteed, even when the pretension is optionally adjusted such that it is small. Thus, the compression can be adjusted individually to the fracture area and to the affected bone tissue and almost independently of the anatomic leverage ratios at the fracture site.

Due to the simple design of the clamping element, the setting device can be manufactured in a particularly cost-effective manner. Thereby, the field of application of compression-producing settings or fixations for the acceleration of the healing process is extended with respect to the potential circle of patients on the one hand and also to relatively uncritical bone fractures on the other hand.

The setting or fixation device according to the invention comprises at least one clamping element and at least two fixing means, preferably cortical screws, which can be placed into the bone in the region of the ends of the fracture, wherein by means of the extension element a predetermined tensile stress can be generated between the fixing means which are enclosed by the continuous loop.

The invention provides that the compression can be generated at a fracture site with the aid of the tensioned continuous loop. On the one hand, the continuous loop extends around the fixing means which are inserted into the opposite ends of the fracture, and, on the other hand, it extends around two opposite ends of the extension element which extends between the fixing means. As the tension of the continuous loop can be adjusted via the regulation of the length of the extension element, tolerances with regard to the distance of the fixing means can be compensated and the compression can be readjusted.

Advantageous further developments are described in the dependent claims.

According to one embodiment, the continuous loop can consist of a wire-like or cord-like material having a substantially constant cross-section over the circumference of the continuous loop. Thus, a flexible formation of the continuous loop and an evenly distributed surface load in the cross-section of the continuous loop over the circumference thereof are ensured.

According to one embodiment, the extension element can furthermore be arranged between the two fixing elements in such a manner that the continuous loop is subdivided into two sections being substantially of the same size, wherein the one fixing means, respectively, is at least partially enclosed by a loop portion which is furthest from the extension element. Hence, the tension or stress is evenly spread onto the loop portions, and the extension element occupies a secure position with regard to a slipping thereof in the circumferential direction of the continuous loop.

In one embodiment, the extension element can comprise two slides with a threaded section, and a threaded sleeve arranged therebetween, wherein preferably one of the slides has a left-hand thread section and the other slide has a right-hand thread section, and wherein, complementary to these, the threaded sleeve has a left-hand thread on the one hand and a right-hand thread on the other hand. In this way, the regulation of the length or the adjustment of the compression can be carried out in a particularly simple manner by a turning of the threaded sleeve which always remains centrically.

In one embodiment, the slide can further comprise a circular section with a circumferential groove for guiding the continuous loop, by means of which the continuous loop is secured against a slipping-off from the slide. Consequently, a slipping-off of the slides of the extension element in the tangential direction of the cross-section of the continuous loop is prevented.

The setting or fixation device according to the invention can additionally also comprise at least one clamping sleeve inside which a fixing means can be received, wherein the clamping sleeve is enclosed at least partially by the continuous loop. The clamping sleeve forms a receiving section for the reception of the continuous loop at the fixing means. By the separate formation of a sleeve element and of the fixing means, the use of standardized fixing means which are obtainable for a reasonable price is possible.

In a further embodiment, the clamping sleeve (2) can comprise two cranks at the end faces thereof. Thus, a coming-off of the continuous loop in the axial direction of the clamping head can be avoided.

According to an exemplary embodiment, the clamping sleeve can comprise at least one groove for guiding the continuous loop, by means of which the continuous loop is secured against a slipping in the axial direction of the clamping sleeve.

At the peripheral area of the clamping sleeve, several parallel-running grooves can be formed in which several continuous loops can be guided side by side.

Thus, a connection point is provided by which the combination of several clamping elements, for instance also of clamping elements with different dimensions or orientations, is rendered possible. Therefore, the setting device according to the invention can easily and individually be adapted to the structure of a fracture, in particular of a comminuted fracture, as well as to the local anatomic conditions.

As compared with a plurality of individual, conventional bone plates, by the combination of several clamping elements the number of the required fastening points can be reduced. This is particularly advantageous for small bone fragments, and, moreover, also reduces the surgical expenditure enormously. In comparison with individually manufactured bone plates, by the modular configuration possibility a rapid treatment of complicated fractures can be achieved.

The healing process of a bone fracture can further be assisted when the supporting cortical layer of the bone will be subjected to loads after a certain time in order to regain again a load-bearing function, as is for instance also the case after the removal of a plaster splinting. In case of a conventional setting, however, a part of the load-bearing function will permanently be taken over by the rigid bone plate.

In accordance with one aspect of the invention, the setting or fixation device can comprise elements which are made of an absorbable synthetic material, i.e. of a material which will be decomposed by the surrounding body tissue. Absorbable synthetic materials have, however, relatively brittle material properties. Consequently, they are only suitable to a limited extent for the formation of regions which are exposed to mechanical stresses.

Consequently, in one embodiment, the setting or fixation device can comprise at least one clamping sleeve which is formed of an absorbable synthetic material. By the absorption of the clamping sleeve, a clearance is created between the fixing means and the continuous loop, which results in a force decoupling between the fixing means. Therefore, the force transmission between the setting or fixation device and the bone gets lost with the progressing absorption of the sleeve elements, whereby the strains on the bones are increased again.

In a further embodiment, at least one clamping sleeve can be divided radially into two sections, wherein the radially inner section or the radially outer section is made of an absorbable synthetic material. By the absorption of one of the two sections, in the setting device also a force decoupling between the fixing means occurs, as mentioned above. If, preferably, an outer section consists of a metal and an inner section consists of an absorbable synthetic material, by means of the cranks on the end faces of the outer section there still remains a local limitation against a coming-off or popping-off of the continuous loop. Thereby, a detaching of the continuous loop from its installation or a potential impairment or damaging of the adjacent body tissue can be prevented.

According to an exemplary embodiment, adjacent clamping elements can overlap each other in such a manner that the fixing means or the clamping sleeve can be enclosed by the overlapping clamping elements. Thus, setting devices can be realized with a chain-shaped or a star-shaped arrangement of clamping elements. By a chain arrangement, a compression between several bone fragments can be obtained with a low number of fixing means. By a star-shaped arrangement of clamping elements, a multidirectional compression can be applied onto bone fragments with intersecting fracture lines, as for instance in case of a comminuted fracture and in particular a wedge fracture. By the selection of the arrangement of clamping elements and of the connection points, the setting device can be aligned individually to the course of different fracture margins.

BRIEF DESCRIPTION OF THE DRAWINGS

Further embodiments, features, and advantages of the invention will become apparent from the following description of embodiments which is made under reference to the accompanying figures, wherein.

DETAILED DESCRIPTION OF THE INVENTION

Figure 1:
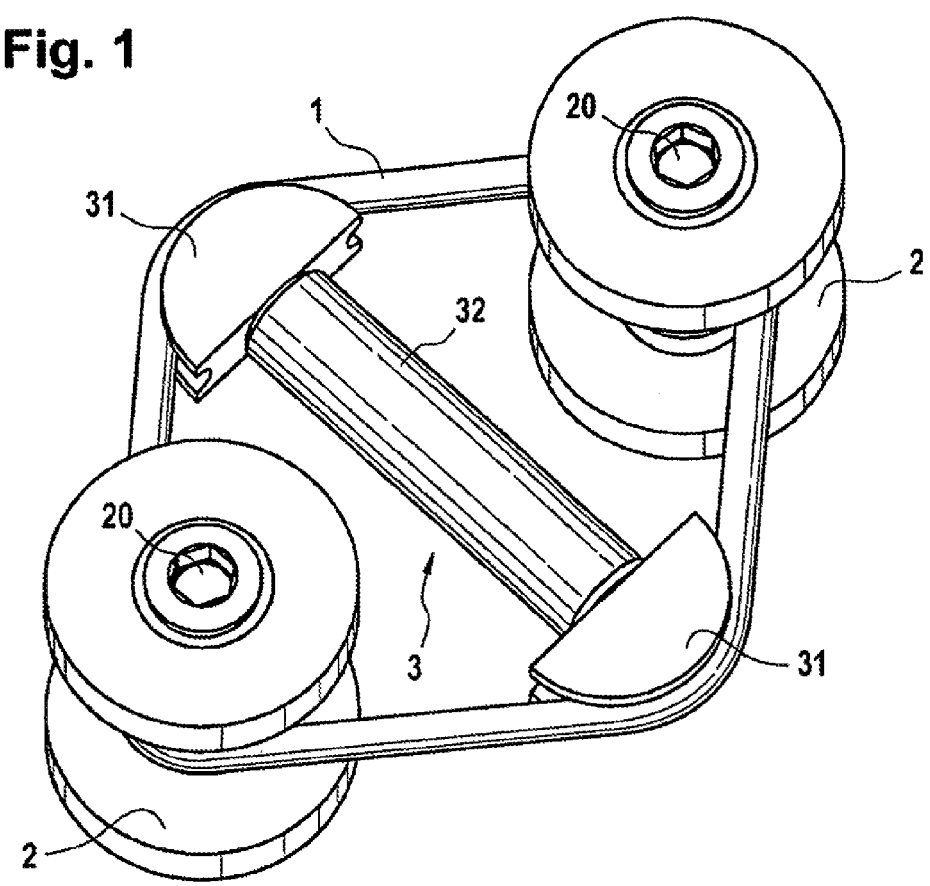
FIG. 1 is a perspective view of a setting or fixation device according to the invention.

FIG. 1 shows a setting or fixation device with two clamping sleeves 2 and a clamping element comprising a continuous loop 1 and an extension element 3. The continuous loop 1 extends around the two clamping sleeves 2 and is stretched out by the extension element 3 into a rhomboidal shape. Inside the two clamping sleeves 2 there are received fixing means 20 which will be inserted into the opposite ends of the fracture of the affected bone. The extension element 3 has a threaded sleeve 32 which connects two slide elements 31 via two oppositely oriented or counter-rotating threaded sections and arranges them in a spaced apart manner such that they are movable or adjustable with respect to each other.

The continuous loop 1 is for instance formed from a wire rope. As the continuous loop 1 is relatively inelastic, i.e. has a steep stress-strain curve, optionally small tensions are sufficient for a secure setting or fixation. Consequently, the permanent compression can be adjusted individually—and almost independently of the anatomic leverage ratios at the fracture site—to a range which is advantageous for the fracture area or the concerned bone tissue. In doing so, also deviations of the distance of the fastening points, which are caused by dimensional tolerances, the anatomic conditions or by the courses of the fracture margins, are compensated for.

The fixing means 20 can be a surgical implant, as for instance a bone nail, a bone screw and in particular a cortical screw, which is placed into the bone. In this connection, the thickness of the corticalis of the different bones differs substantially according to the bones, for instance at a thigh bone or a jaw bone. There are available cortical screws with staggered diameters and lengths for the various applications, which are standardized according to ISO 5835: 1991 or ASTM: F 543-07.

Principally, in this connection there are not given any fixed specifications between the size of the setting or fixation device and the respective bone, though a proportional dimensioning of the cross-section of the continuous loop or of the extension element 3 with respect to the used screw system is conceivable. From the practical medical technology there can be approximately established a connection between the nominal diameter of the cortical or spongiosa screw and the field of application, which is listed in the following table:

| Screw System | Field of Application |
| --- | --- |
| HA 1.5 Cortical | oral and maxillofacial surgery |
| HA 2.0 Cortical | cranio; foot surgery; hand surgery |
| HA 2.5 Cortical | cranio; foot surgery; trauma |
| HA 3.5 Cortical | thorax; lower back; arm surgery |
| HA 4.0 Cortical | thorax; spinal column; hip and pelvis area |
| HA 4.5 Cortical | leg surgery; trunk; fibula; shoulder |
| HA 5.0 Cortical | leg surgery; tibia; femur |
| HB 4.0 Spongiosa | depending on the load case |
| HB 6.0 Spongiosa | depending on the load case |

The selection of the dimensioning and positioning of the screw system as well as of the setting device also depends on the type of fracture (e.g. transverse fracture, oblique fracture) and on the location of a fracture, from which there will result different load cases.

Thus, in case of diaphyseal fractures, in most cases cortical systems will be used, as here no spongiosa portion is given. On the other hand, in case of fractures near a joint, very often spongiosa systems will be used, as the percentage of the spongiosa is very high in this area. Spongiosa screws have a higher percentage contact area, as they have a larger core diameter for the same nominal diameter. In case of joint fractures, i.e. fractures with the participation of the articular surface, there will be used cortical systems as well as spongiosa systems in dependence on the local anatomic conditions. In case of a multifold fracture, also both systems can be used.

Furthermore, apart from a single, i.e. monocortical fixation possibility, also bicortical systems can be provided in which the screw is fixed through the bone in both cortical regions.

Figure 2:
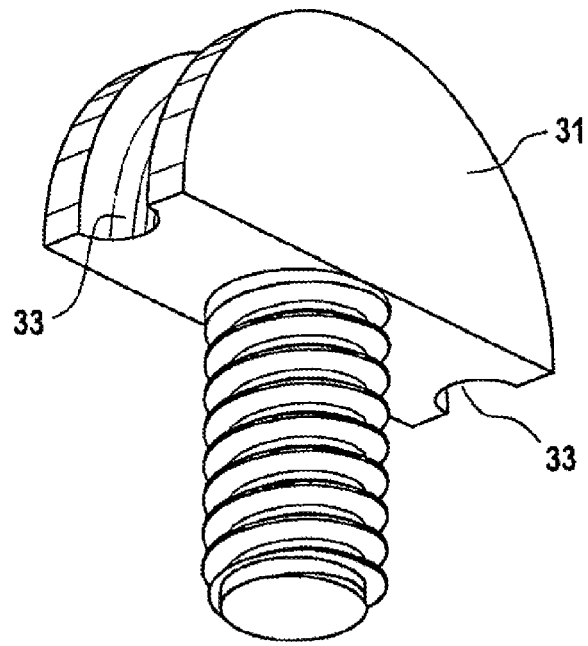
FIG. 2 is a perspective view of a slide of the extension element.

After the fixing means 20 being inserted into the bone and the clamping sleeves 2 being fixed, the continuous loop 1 is placed around them. Then the extension element 3 is positioned and expanded in the continuous loop 1 perpendicularly to a line through the two fastening points. By a turning of the threaded sleeve 32, the oppositely-oriented threaded sections of the slide elements 31 are moved out of the threaded sleeve 32 on both sides so that the extension element 3 becomes longer. When the circumferential groove 33 of the slide elements 31, which is shown in FIG. 2, abuts at the continuous loop 1, the continuous loop 1 is kept under a tension. In order to facilitate the adjustment of the regulation of the length, there is for instance provided a millimeter indication or the like at the threaded sections of the slide elements 31 or at a window opening in the threaded sleeve 32.

Furthermore, the fixing means 20 can comprise a section with a clamping sleeve 2. Upwards and downwards, the clamping sleeve 2 comprises a crank at the end faces thereof, which prevents a coming-off or popping-off of the continuous loop 1 in the axial direction of the fixing means 20. The clamping sleeve 2 can for instance be formed separately and will be combined with a cortical screw which is received in a through-hole of the clamping sleeve 2.

Figure 3:
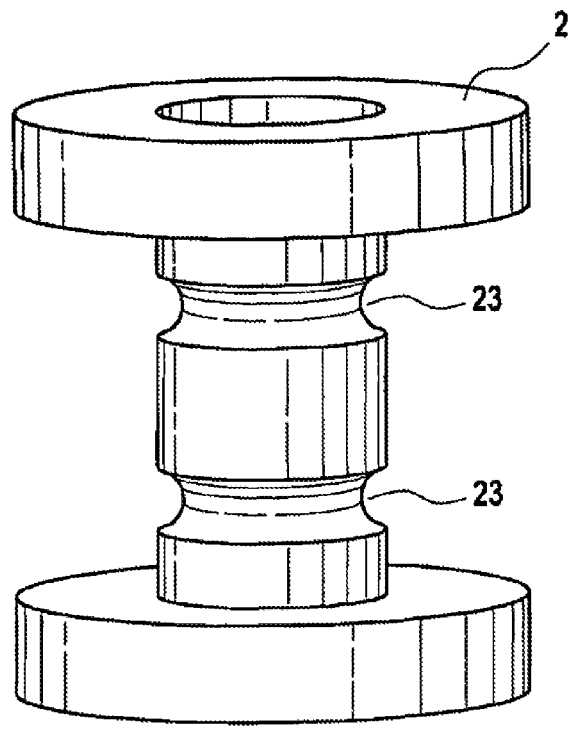
FIG. 3 is a perspective view of a clamping sleeve.

FIG. 3 shows a clamping sleeve 2 with cranks at the end faces thereof and two parallel-running grooves 23 for the guidance of continuous loops 1. Thus, depending on the number of the grooves 23, two or more different clamping elements can be connected with each other at a fastening point.

Figure 4:
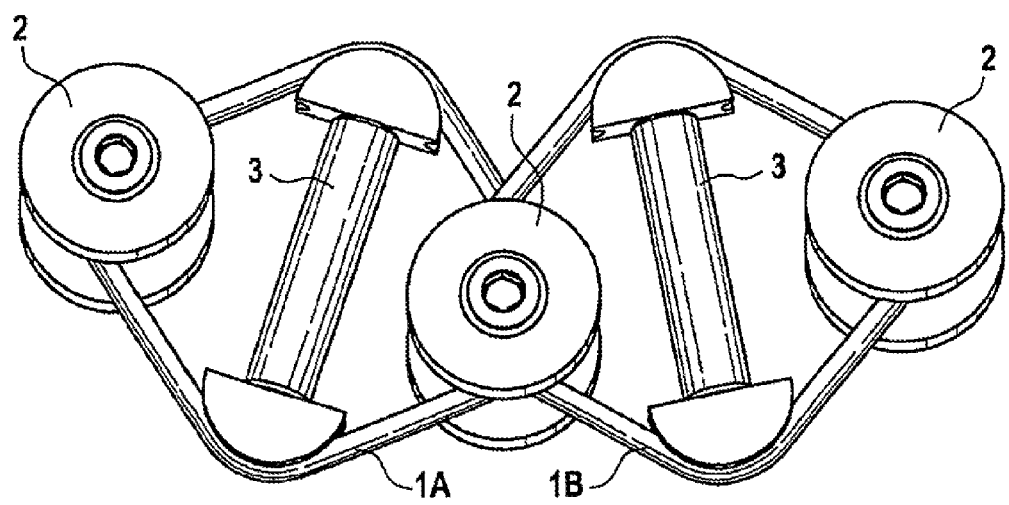
FIG. 4 is a perspective view of a chain arrangement of two clamping elements.

By said structure, the present setting or fixation device can also be expanded to a chain-shaped arrangement, as is shown in FIG. 4, or to a star-shaped arrangement or to any combination of chain-like or star-shaped arrangements. Depending on the number of the grooves 23 in the clamping sleeve 2 or on their width between the cranks at the end faces, for example a star-shaped arrangement of three or more clamping elements can be formed. In this combination, possibly a clamping sleeve 2 without any inserted cortical screw or the like can be enclosed by the continuous loops 1.

Figure 5:
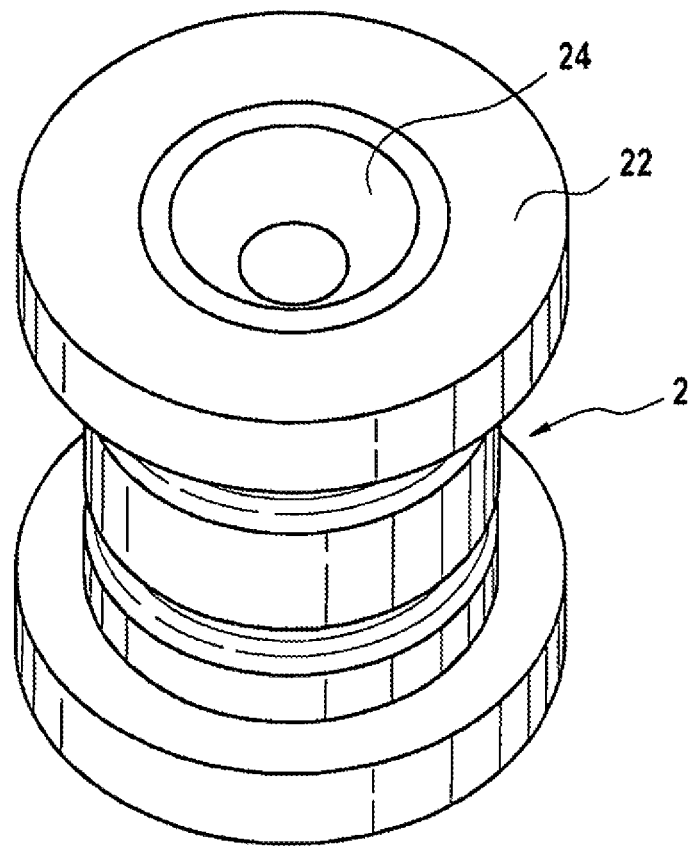
FIG. 5 is a perspective view of a radially divided clamping sleeve with an absorbable section.

The clamping sleeve 2 in FIG. 5 comprises a radially inner section 24 inside which a cortical screw can be received. The radially inner section 24 is inserted into the radially outer section 22 of the clamping sleeve 2 by means of a fit, preferably a press fit. The radially inner section 24 can be formed of an absorbable synthetic material, and the radially outer section 22 can be formed of a metal, or vice versa.

When, for instance, the radially inner section 24 is absorbed, an empty space is created in the clamping sleeve 2 around the cortical screw, which corresponds to the section 24. As a result thereof, the clamping sleeves 2 are displaced and the circumference for the enclosing of the spaced-apart clamping sleeves 2 is reduced. The tension of the continuous loop 1 is released so that a force decoupling between the fixing means 20 takes place. Thus, the bone will be subjected again to an increasing strain.

The elements of the setting or fixation device are manufactured from biocompatible materials and can comprise a hybrid structure, i.e. a section-wise combination of several materials.

As a basic material for the elements of the setting device, for instance metals from the group consisting of: X42CrMo15, X100CrMo17, X2CrNiMnMoNNb21-16-5-3, X20Cr13, X15Cr13, X30Cr13, X46Cr13, X17CrNi16-2, X14CrMoS17, X30CrMoN15-1, X65CrMo 17-3, X55CrMo14, X90CrMoV18, X50CrMoV15, X 38CrMo V15, G-X 20CrMo13, X39CrMo17-1, X40CrMoVN16-2, X105CrMo17, X20CrNiMoS13-1, X5CrNi18-0, X8CrNiS18-9, X2CrNi19-11, X2CrNi18-9, X10CrNi18-8, X5CrNiMo17-12-2, X2CrNiMo17-12-2, X2CrNiMoN25-7-4, X2CrNiMoN17-13-3, X2CrNiMo17-12-3, X2CrNiMo18-14-3, X2CrNiMo18-15-3; X 2 CrNiMo 18 14 3, X13CrMnMoN18-14-3, X2CrNiMoN22136, X2CrNiMnMoNbN21-9-4-3, X4CrNiMnMo21-9-4, X105CrCoMo18-2, X6CrNiTi18-10, X5CrNiCuNb16-4, X3CrNiCuTiNb12-9, X3CrNiCuTiNb12-9, X7CrNiAl17-7, CoCr20Ni15Mo, G-CoCr29Mo, CoCr20W15Ni, Co-20Cr-15W-10Ni, CoCr28MoNi, CoNi35Cr20Mo10, Ti1, Ti2, Ti3, Ti4, Ti-5Al-2,5Fe, Ti-5Al-2,5Sn, Ti-6Al-4V, Ti-6Al-4V ELI, Ti-3Al-2,5V (Gr9), 99,5Ti, Ti-12Mo-6Zr-2Fe, Ti-13,4Al-29Nb, Ti-13Nb-13Zr, Ti-15Al, Ti-15Mo, Ti-15Mo-5Zr-3Al, Ti-15Sn, Ti-15Zr-4Nb, Ti-15Zr-4Nb-4Ta, Ti-15Zr-4Nb-4Ta-0,2Pd, Ti-29Nb-13Ta-4,6Zr, Ti-30Nb-10Ta-5Zr, Ti-35,5Nb-1,5Ta-7,1Zr, Ti-35Zr-10Nb, Ti-45Nb, Ti-30Nb, Ti-30Ta, Ti-6Mn, Ti-5Zr-3Sn-5Mo-15Nb, Ti-3Al-8V-6Cr-4Zr-4Mo, Ti-6Al-2Nb-1Ta-0,8Mo, Ti-6Al-4Fe, Ti-6Al-4Nb, Ti-6Al-6Nb-1Ta, Ti-6Al-7Nb, Ti-6Al-4Zr-2Sn-2Mo, Ti-8,4Al-15,4Nb, Ti-8Al-7Nb, Ti-8Al-1Mo-1V, Ti-11Mo-6Zr-4Sn, can be used.

Furthermore, polymers from the group consisting of: MBS, PMMI, MABS, CA, CTA, CAB, CAP, COC, PCT, PCTA, PCTG, EVA, EVAL, PTFE, ePTFE, PCTFE, PVDF, PVF, ETFE, ECTFE, FEP, PFA, LCP, PMMA, PMP, PHEMA, Polyamide 66, Polyamide 6, Polyamide 11, Polyamide 2, PAEK, PEEK, PB, PC, PPC, PETP, PBT, MDPE, LDPE, HDPE, UHMWPE, LLDPE, PI, PAI, PEI, PIB, POM, PPO, PPE, PPS, PP, PS, PSU, PESU, PVC, PVC-P, PVC-U, ABS, SAN, TPE-U, TPE-A, TPE-E, PVDC, PVA, SI, PDMS, EPM, EP, UF, MF, PF, PUR, UP, PEBA, PHB, PLA, PLLA, PDLA, PDLLA, PGL, PGLA, PGLLA, PGDLLA, PGL-co-poly TMC, PGL-co-PCL, PDS, PVAL, PCL, Poly-TMC, PUR (linear), NiTi Superelastic, NiTi Shape Memory, can be used.

Furthermore, also ceramics from the group consisting of: $Al_2O_3$ (alumina oxide), Y-TZP (zirconium oxide ceramic), AMC (alumina matrix composite), HA (hydroxyl apatite), TCP (tricalcium phosphate), Ceravital (glass ceramic/Bioglas®), FZM/K (zirconium oxide, partially stabilized), TZP-A (zirconium oxide ceramic), ATZ (alumina-toughened zirconia), C799 (alumina oxide ceramic), Schott 8625 (transponder glass), can be used.

Furthermore, also any combinations thereof can be used.

Apart from the shown embodiments, the invention also allows for further design approaches.

There is, for instance, possible one embodiment of the setting or fixation device according to the invention in which the clamping sleeves 2 consist completely of an absorbable synthetic material. When the clamping sleeves 2 are absorbed by the surrounding body tissue, corresponding empty spaces are created. As described above, the force transmission of the setting or fixation device vanishes with the progressing absorption of the clamping sleeves 2, whereby the load onto the bones increases again.

Furthermore, it is also possible to provide at the extension element 3 an axial guide between the slide elements 31 instead of a threaded sleeve, wherein at the axial guide a regulation of the length can be carried out by means of a snap-in locking system, a lockable eccentric, a toggle, a centrally supported steering arm or similar mechanisms.

Furthermore, it is also possible to provide an indicator at the extension element 3, e.g. a scale, which, either on the basis of a removed length or on the basis of a compressive stress which are measured at the extension element, allows for an optical conclusion for the adjustment of a suitable tension of the setting device.

Moreover, it is also possible that the extension element 3 can be pretensioned in the longitudinal direction by means of a compression spring or by another similar elastic element.

By the above-discussed invention, a clamping element for setting or fixation of a bone fracture is provided, which comprises a flexible and substantially non-plastically deformable continuous loop. Inside said continuous loop, at least two fixing means, preferably cortical screws, can be pushed through. The clamping element further comprises an extension element of alterable length that can be inserted into and is expandable inside the continuous loop. By means of the extension element, a predetermined tensile stress can be generated over the circumference of the continuous loop, so that, in doing so, forces which are directed towards each other are applied to the fixing means. Furthermore, according to the invention there is also provided a setting or fixation device for the use of the clamping element.

What is claimed is:

1. A clamping element for bone fractures, wherein the clamping element comprises
   (i) a flexible and substantially non-plastically deformable continuous loop, inside which at least two fixing elements can be pushed through,
   (ii) an extension element of alterable length and comprising two slides arranged on end sides of the extension element for guiding the continuous loop, which extension element can be inserted into and is expandable inside the continuous loop in such a manner that, in order to apply forces directed towards each other onto the at least two fixing elements when pushed through the continuous loop, a predetermined tensile stress can be generated over a circumference of the continuous loop by regulating the length of the extension element, and (iii) at least one clamping sleeve inside which a fixing element can be received, the at least one clamping sleeve being enclosed at least partially by the continuous loop and having two cranks at end faces thereof;

and wherein a distance between the two slides can be adjusted in a longitudinal direction of the extension element by threaded sections formed on the slides.

2. The clamping element of claim 1, wherein the at least two fixing elements are cortical screws.

3. The clamping element of claim 1, wherein the continuous loop consists of a wire-like or cord-like material having a substantially constant cross-section over the circumference of the continuous loop.

4. The clamping element of claim 1, wherein the extension element can be arranged between the two fixing elements in such a manner that the continuous loop is subdivided into two sections of substantially equal size, each fixing element being at least partially enclosed by a loop section which is furthest from the extension element.

5. The clamping element of claim 1, wherein the extension element further comprises a threaded sleeve arranged between the two slides.

6. The clamping element of claim 5, wherein one of the two slides has a left-hand thread section and the other slide has a right-hand section, and wherein, complementary thereto, the threaded sleeve has a left-hand thread on the one hand and a right-hand thread on the other hand for adjusting the distance between the two slides by cooperative interaction of the thread sections formed on the slides and the threads formed on the threaded sleeve.

7. The clamping element of claim 5, wherein each slide has a circular section with a circumferential groove for guiding the continuous loop, by means of which the continuous loop is secured against a slipping-off from the slide.

8. A clamping element for bone fractures, wherein the clamping element comprises (i) a flexible and substantially non-plastically deformable continuous loop, inside which at least two fixing elements can be pushed through, (ii) an extension element of alterable length and comprising two slides arranged on end sides of the extension element for guiding the continuous loop, which extension element can be inserted into and is expandable inside the continuous loop in such a manner that, in order to apply forces directed towards each other onto the at least two fixing elements when pushed through the continuous loop, a predetermined tensile stress can be generated over a circumference of the continuous loop by regulating the length of the extension element, and (iii) at least one clamping sleeve inside which a fixing element can be received, the at least one clamping sleeve being enclosed at least partially by the continuous loop and (a) being made of absorbable synthetic material or (b) being radially divided into two sections, a radially inner section or a radially outer section being made of absorbable synthetic material;

and wherein a distance between the two slides can be adjusted in a longitudinal direction of the extension element by threaded sections formed on the slides.

9. The clamping element of claim 8, wherein the at least two fixing elements are cortical screws.

10. The clamping element of claim 8, wherein the continuous loop consists of a wire-like or cord-like material having a substantially constant cross-section over the circumference of the continuous loop.

11. The clamping element of claim 8, wherein the extension element can be arranged between the two fixing elements in such a manner that the continuous loop is subdivided into two sections of substantially equal size, each fixing element being at least partially enclosed by a loop section which is furthest from the extension element.

12. The clamping element of claim 8, wherein the extension element further comprises a threaded sleeve arranged between the two slides.

13. The clamping element of claim 12, wherein one of the two slides has a left-hand thread section and the other slide has a right-hand section, and wherein, complementary thereto, the threaded sleeve has a left-hand thread on the one hand and a right-hand thread on the other hand for adjusting the distance between the two slides by cooperative interaction of the thread sections formed on the slides and the threads formed on the threaded sleeve.

14. The clamping element of claim 12, wherein each slide has a circular section with a circumferential groove for guiding the continuous loop, by means of which the continuous loop is secured against a slipping-off from the slide.

15. A fixation device for a bone fracture, wherein the device comprises (A) at least one clamping element according to claim 1, and (B) the at least two fixing elements which can be inserted into a bone in a region of ends of a fracture, wherein by means of the extension element, a predetermined tensile stress can be generated between the fixing elements which are pushed through and enclosed by the at least one continuous loop assigned to the corresponding extension element.

16. The fixation device of claim 15, wherein the at least two fixing elements are cortical screws.

17. The fixation device of claim 15, wherein the at least one clamping sleeve comprises at least one groove for guiding the continuous loop, by means of which the continuous loop is secured against a slipping in axial direction of the at least one clamping sleeve.

18. A fixation device for a bone fracture, wherein the device comprises (A) at least one clamping element according to claim 8, and (B) the at least two fixing elements which can be inserted into a bone in a region of ends of a fracture, wherein by means of the extension element, a predetermined tensile stress can be generated between the fixing elements which are pushed through and enclosed by the at least one continuous loop assigned to the corresponding extension element.

19. The fixation device of claim 18, wherein the at least two fixing elements are cortical screws.

20. A fixation device for a bone fracture, wherein the device comprises (A) a plurality of clamping elements, a clamping element comprising (i) a flexible and substantially non-plastically deformable continuous loop, inside which at least two fixing elements can be pushed through, (ii) an extension element of alterable length and comprising two slides arranged on end sides of the extension element for guiding the continuous loop, which extension element can be inserted into and is expandable inside the continuous loop in such a manner that, in order to apply forces directed towards each other onto the at least two fixing elements when pushed through the continuous loop, a predetermined tensile stress can be generated over a circumference of the continuous loop by regulating the length of the extension element, and (iii) at least one clamping sleeve inside which a fixing element can be received, and wherein a distance between the two slides can be adjusted in a longitudinal direction of the extension element by threaded sections formed on the slides;

(B) the at least two fixing elements which can be inserted into a bone in a region of ends of a fracture, wherein by means of the extension element, a predetermined tensile stress can be generated between the fixing elements which are pushed through and enclosed by the at least one continuous loop assigned to the corresponding extension element, and wherein adjacent clamping elements overlap each other in such a manner that the same fixing elements or the same clamping sleeve can be jointly enclosed by the overlapping clamping elements.

* * * * *